United States Patent
Cook et al.

(10) Patent No.: US 9,457,136 B2
(45) Date of Patent: Oct. 4, 2016

(54) WRAP AND RELATED SYSTEMS AND METHODS

(71) Applicant: Sunshine Heart Company Pty, Ltd., Clontarf (AU)

(72) Inventors: Martin Cook, Eden Prairie, MN (US); Tolga Tas, Shoreview, MN (US); Khamporn Phanthanivong, Brooklyn Park, MN (US); Warrick Heald, Sydney (AU); Kenneth Lee, Eden Prairie, MN (US); William Peters, Auckland (NZ); Scott Miller, Sydney (AU)

(73) Assignee: SUNSHINE HEART COMPANY PTY, LTD, New South Wales (AU)

( * ) Notice: Subject to any disclaimer, the term of this patent is extended or adjusted under 35 U.S.C. 154(b) by 0 days.

(21) Appl. No.: 14/705,691

(22) Filed: May 6, 2015

(65) Prior Publication Data

US 2015/0320415 A1     Nov. 12, 2015

Related U.S. Application Data

(60) Provisional application No. 61/989,280, filed on May 6, 2014.

(51) Int. Cl.
| | | |
|---|---|---|
| *A61N 1/362* | (2006.01) | |
| *A61M 1/10* | (2006.01) | |
| *A61B 17/04* | (2006.01) | |
| *A61M 1/12* | (2006.01) | |
| *A61B 17/06* | (2006.01) | |

(52) U.S. Cl.
CPC .......... *A61M 1/107* (2013.01); *A61B 17/0482* (2013.01); *A61B 17/06166* (2013.01); *A61M 1/1067* (2013.01); *A61M 1/122* (2014.02); *A61M 1/12* (2013.01); *A61M 2205/04* (2013.01); *A61M 2205/3327* (2013.01); *A61M 2210/127* (2013.01)

(58) Field of Classification Search
CPC .................. A61B 17/0482; A61B 17/06166; A61M 1/107; A61M 1/122; A61M 2205/04; A61M 2205/3327; A61M 2210/127; A61M 1/12; A61M 1/1067
See application file for complete search history.

(56) References Cited

U.S. PATENT DOCUMENTS

| | | | |
|---|---|---|---|
| 2004/0073080 A1* | 4/2004 | Peters et al. | .......... 600/18 |
| 2007/0135677 A1 | 6/2007 | Miller et al. | |
| 2007/0167898 A1 | 7/2007 | Peters et al. | |
| 2010/0070019 A1 | 3/2010 | Shalev | |
| 2010/0292528 A1 | 11/2010 | De Plater et al. | |

FOREIGN PATENT DOCUMENTS

WO    WO 0224255 A1    3/2002

\* cited by examiner

*Primary Examiner* — George Manuel
(74) *Attorney, Agent, or Firm* — Schwegman Lundberg & Woessner, P.A.

(57) ABSTRACT

The inventions disclosed herein relate to systems for securing medical devices to a blood vessel of a patient, including securing a vessel deforming component to a blood vessel. Certain embodiments relate to wraps configured to be secured around a blood vessel, including wraps configured to hold a vessel deformer adjacent a blood vessel, and further including, for example, a pulsatile balloon adjacent the aorta.

17 Claims, 7 Drawing Sheets

WRAP AND RELATED SYSTEMS AND METHODS

CROSS-REFERENCE TO RELATED APPLICATION

This application claims the benefit under 35 U.S.C. §119 (e) to U.S. Provisional Application 61/989,280, filed May 6, 2014 and entitled "Wrap and Related Systems and Methods, which is hereby incorporated herein by reference in its entirety.

FIELD OF THE INVENTION

The various embodiments disclosed herein relate to heart assist devices and systems, and more specifically to a wrap configured to be secured around a blood vessel. Specific embodiments include wraps configured to hold a vessel deformer adjacent an arterial vessel, including, for example, a pulsatile balloon adjacent the aorta.

BACKGROUND OF THE INVENTION

Certain mechanical heart assist device systems include vessel deforming components in the form of inflatable balloons or chambers which form part of implantable counter-pulsation heart assist devices. In certain specific embodiments, the vessel deforming components are cyclically inflated and deflated and used to compress the patient's ascending aorta during diastole and release the compression during systole, thereby assisting with pushing blood to the patient's body.

The balloon or chamber are generally secured to the aorta (or other blood vessel) by a substantially flexible, non-elastic, non-distensible wrap or sheath, which is secured around a section of the aorta with the balloon or chamber therebetween. For the heart assist device to function efficiently, it is necessary that the wrap be a snug fit around the aorta when the balloon or chamber is deflated.

In use, the securing of the balloon to the aorta with the wrap can be awkward or difficult. That is, it can be difficult to position a wrap around the aorta during surgery for various reasons, including the fact that wrap is made of a flexible material that is not easily directed around and between various organs and vessels in the chest cavity. An additional complication can arise based on the size of the patient's aorta—the variance in aorta size depending on the patient can result in a situation in which the wrap is not the optimal size for securing the vessel deforming component to the aorta. Further, another difficulty relates to affixing the fastening components to the wrap. Attempting to hold the wrap in position around the aorta while securing the wrap in that position in a permanent fashion can be very difficult to accomplish with two hands.

There is a need in the art for an improved wrap and improved methods of securing that wrap to the target vessel.

BRIEF SUMMARY OF THE INVENTION

Discussed herein are various systems for coupling a vessel deforming component to a blood vessel, including specific wrap embodiments for use in those systems.

In Example 1, a system for coupling a vessel deforming component to a blood vessel comprises a wrap and a vessel deforming component operably coupled to the wrap. The wrap comprises a body, size markings disposed on the body, and a plurality of pairs of sutures extending from a proximal end of the body, wherein each of the sutures comprises a needle disposed at a distal end of the suture.

Example 2 relates to the system according to Example 1, further comprising a suture carrier comprising an elongate body, a plurality of foldable sections defined in the elongate body, at least one engagement structure associated with each foldable section, and insertion markings disposed on at least one of the foldable sections. Each of the at least one engagement structures is removably coupleable with the needle of one of the sutures of the plurality of pairs of sutures. The insertion markings are configured to indicate insertion positions of the plurality of pairs of sutures.

Example 3 relates to the system according to Example 1, wherein each pair comprises a color that is different from either adjacent pair of sutures. Example 4 relates to the system according to Example 1, wherein the body comprises non-traumatic outer edges.

Example 5 relates to the system according to Example 4, wherein the non-traumatic edges comprise a coated polymer, a coated elastomer, or a soft, stretchable fabric.

Example 6 relates to the system according to Example 1, wherein the wrap further comprises a lead member coupled to a distal end of the body.

In Example 7, a system for coupling a vessel deforming component to a blood vessel comprises a wrap and a suture carrier comprising an elongate structure. The wrap comprises a body, size markings disposed on the body, and a plurality of sutures extending from a proximal end of the body. The elongate structure comprises a plurality of foldable sections, wherein each of the foldable sections comprises at least one engagement structure.

Example 8 relates to the system according to Example 7, wherein the plurality of sutures are arranged in a plurality of pairs, wherein each suture comprises a needle disposed at a distal end of the suture.

Example 9 relates to the system according to Example 8, wherein each pair comprises a color that is different from either adjacent pair of sutures.

Example 10 relates to the system according to Example 7, wherein at least one of the foldable sections comprises insertion markings configured to indicate a sequential order of insertion of the plurality of sutures.

Example 11 relates to the system according to Example 7, wherein the body comprises non-traumatic outer edges.

Example 12 relates to the system according to Example 11, wherein the non-traumatic edges comprise a coated polymer, a coated elastomer, or a soft, stretchable fabric.

Example 13 relates to the system according to Example 7, wherein the wrap further comprises a lead member coupled to a distal end of the body.

Example 14 relates to the system according to Example 7, further comprising a vessel deforming component operably coupled to the wrap.

In Example 15, a method of coupling a vessel deforming component to a blood vessel comprises positioning a lead member behind an aorta of a patient, urging the lead member distally around the aorta such that the wrap is positioned around the aorta, sequentially removing sutures of the plurality of sutures from engagement structures in a suture carrier and sequentially inserting the sutures into a desired location on the size markings, and tightening the sutures. The lead member is operably coupled to a distal end of a wrap. The wrap comprises a body, size markings disposed on the body, and a plurality of sutures extending from a proximal end of the body.

Example 16 relates to the method according to Example 15, further comprising removing the lead member from the wrap after urging the lead member distally around the aorta.

Example 17 relates to the method according to Example 15, further comprising folding the body of the wrap to narrow a width of the body prior to urging the lead member distally around the aorta and then unfolding the body of the wrap after urging the lead member distally around the aorta.

Example 18 relates to the method according to Example 15, further comprising opening the suture carrier and separating at least one foldable section from the suture carrier prior to sequentially removing sutures.

Example 19 relates to the method according to Example 15, further comprising cutting excess length of the sutures and excess portions of the body after tightening the sutures.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1A:
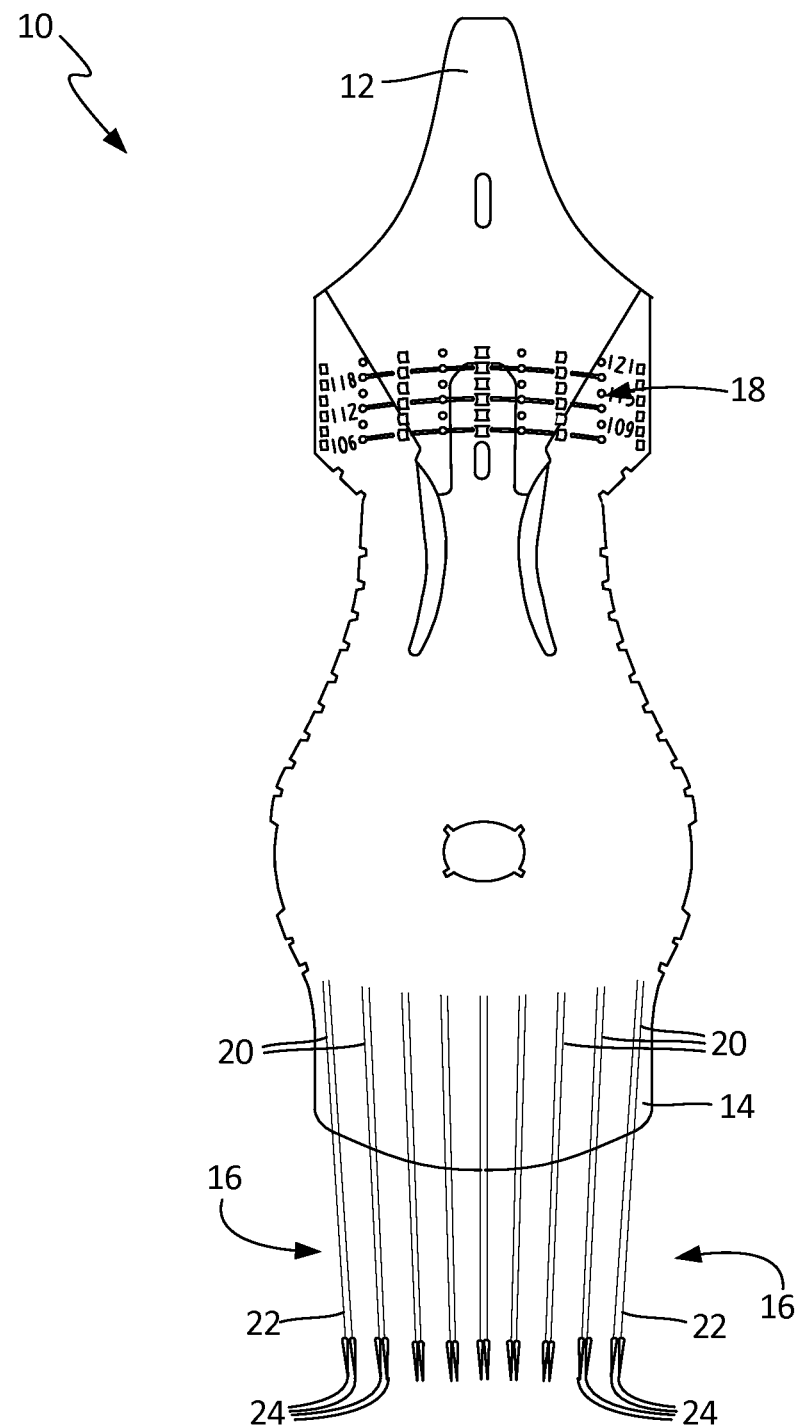
FIG. 1A is a front view of a wrap, according to one embodiment.
Figure 1B:
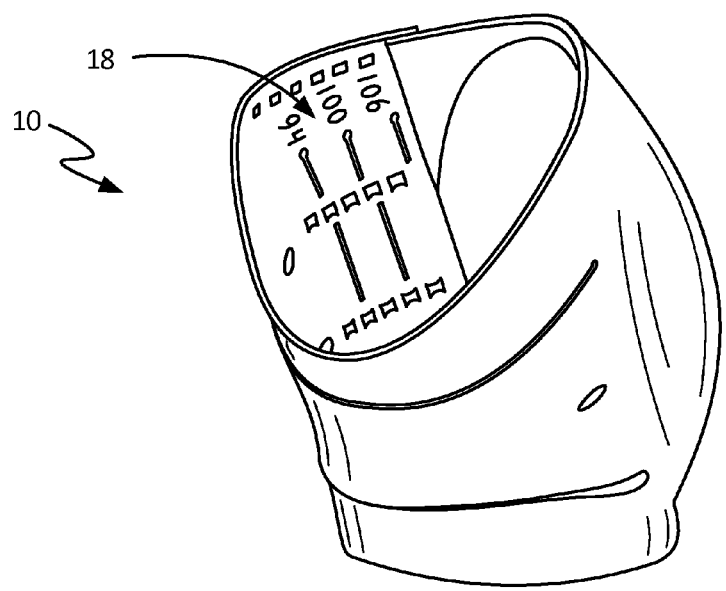
FIG. 1B is a perspective view of the wrap of FIG. 1A.
Figure 1C:
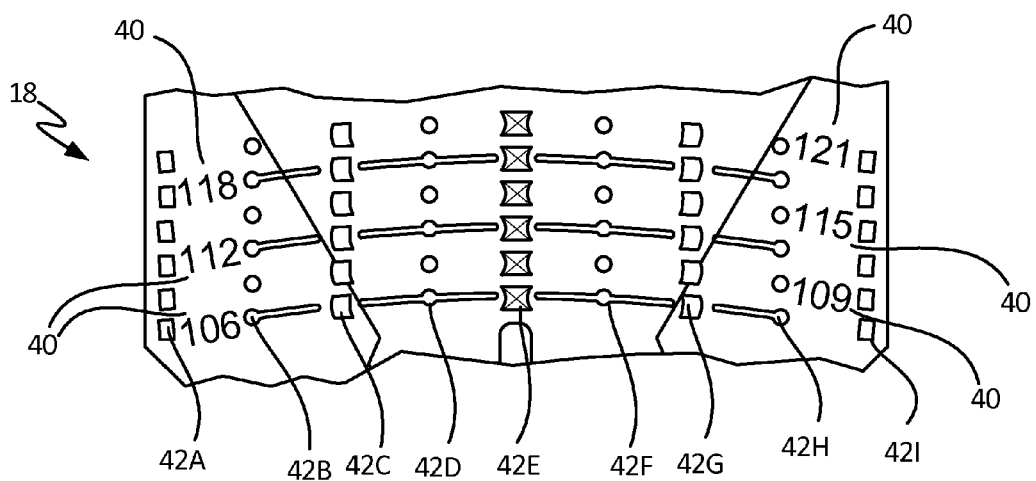
FIG. 1C is an expanded view of the markings of the wrap of FIG. 1A.

The various embodiments disclosed herein relate to improved wraps and improved methods of using such improved wraps to secure a vessel deforming component to or against a patient's blood vessel. FIGS. 1A, 1B, and 1C depict a wrap 10 according to one embodiment having a first end 12 and a second end 14. As best shown in FIG. 1A, this wrap 10 has sutures 16 fixedly attached to the wrap 10 near the second end 14. Further, the wrap 10 has size markings 18 on the wrap 10 near the first end 12.

The sutures 16 in this particular embodiment are arranged in suture pairs as best shown in FIG. 1A, with the proximal end 20 of each suture being fixedly attached to the wrap 10 and the distal end 22 having a needle 24 affixed thereto. Alternatively, the sutures 16 need not be arranged in pairs and can have any known configuration. According to another embodiment, both threads of each pair of sutures 16 are the same color, but each pair has a different color from the adjacent pairs on both sides. In a specific example, there are two suture 16 colors that alternate across the suture 16 pairs such that if a first pair is the first color, then the second pair is the second color and the third pair is the first color, etc. For example, the two suture 16 colors are green and white, according to one embodiment. Alternatively, the two suture 16 colors can be any two different colors. In a further alternative, there are three or more different colors that alternate across the suture 16 pairs.

The size markings 18 are depicted in further detail in FIG. 1C, according to one implementation. The markings 18 are provided to indicate the possible attachment points for the sutures 16, depending on the size of the aorta (or other vessel) around which the wrap 10 is intended to be positioned. That is, the markings 18 are configured to provide for at least two different sets of indicia that mark attachment points for the sutures 16, thereby providing for two different wrap 10 circumferences when the wrap 10 has been secured to the aorta. Alternatively, the markings 18 on the wrap 10 embodiments contemplated herein can have any number of different sets of indicia (described in further detail below), thereby providing for a wrap 10 that can fit around and be secured to vessels of any number of different sizes.

As best shown in FIG. 1C, the markings 18 in this exemplary implementation provide for six different sizes, as shown by the six different numbers 40 (the actual numbers being 106 through 121) and associated indicia discussed below. Alternatively, That is, each number 40 and associated indicia represents a different set of attachment points for the sutures 16 and thus a different size for the wrap 10. For example, the number 106 identifies the set of indicia that constitute the attachment points for the smallest circumference of this wrap 10. The markings for 106 represent nine indicia: a first indicia 42A (in this case, a box), a second indicia 42B (in this case, a dot), a third indicia 42C, a fourth indicia 42D (in this case, another dot), a fifth indicia 42E (in this case, an X-like object), a sixth indicia 42F (in this case, another dot), a seventh indicia 42G, an eighth indicia 42H (in this case, a dot), and a ninth indicia 42I (in this case, a box). The indicia 42A-42I, in some embodiments, identify the set of points or locations where the various sutures 16 can be inserted through the wrap 10 to achieve the desired circumference for the wrap 10 when it is fully secured to the blood vessel using the sutures 16. It is understood that, as shown in FIG. 1C, equivalent indicia are provided for each of the other numbers 40 as well.

In this specific implementation, the nine indicia 42A-42I are shapes that are intended to be attachment points, with each shape 42A-42I being an attachment point for a pair of sutures 16. More specifically, one of the two sutures 16 is inserted along one side of the shape (any one of the shapes 42A-42I) and the other of the two sutures 16 in the pari is inserted along the other side. Alternatively, the attachment points can be represented by any type of shapes or other indicia that indicates whether the sutures 16 should be inserted through the wrap 10. It is also understood that the number of indicia can vary in amount based on the number of sutures 16 to be inserted through the wrap 10.

For purposes of this implementation, the larger the aorta, the greater the number 40 (and thus set of attachment points) that is chosen. Thus, if the aorta is smaller, the number 40 chosen might be 106, 109, or 112, while if the aorta is larger, then a larger number 40 will be chosen.

In one embodiment, the numbers 40 indicate the actual circumference of the wrap 10 when the sutures 16 are attached at that particular number 40. For example, in the specific embodiment depicted in FIG. 1C, the numbers 40 represent the circumference of the wrap 10 in millimeters, with the smallest size being 106 millimeters and the largest size being 121 millimeters.

According to one embodiment, a set of wraps (such as wrap 10) of different sizes can be provided. For example, in one specific implementation, a set of three wraps is provided, with the first wrap having six sizes (sets of attachment points), ranging from 91 to 106 mm, the second wrap having six sizes ranging from 106 to 121 mm, and the third wrap having six sizes ranging from 118 to 133 mm. Alternatively, the set of wraps can have any number of wraps with any number of size ranges to encompass any target blood vessel size.

Figure 2A:
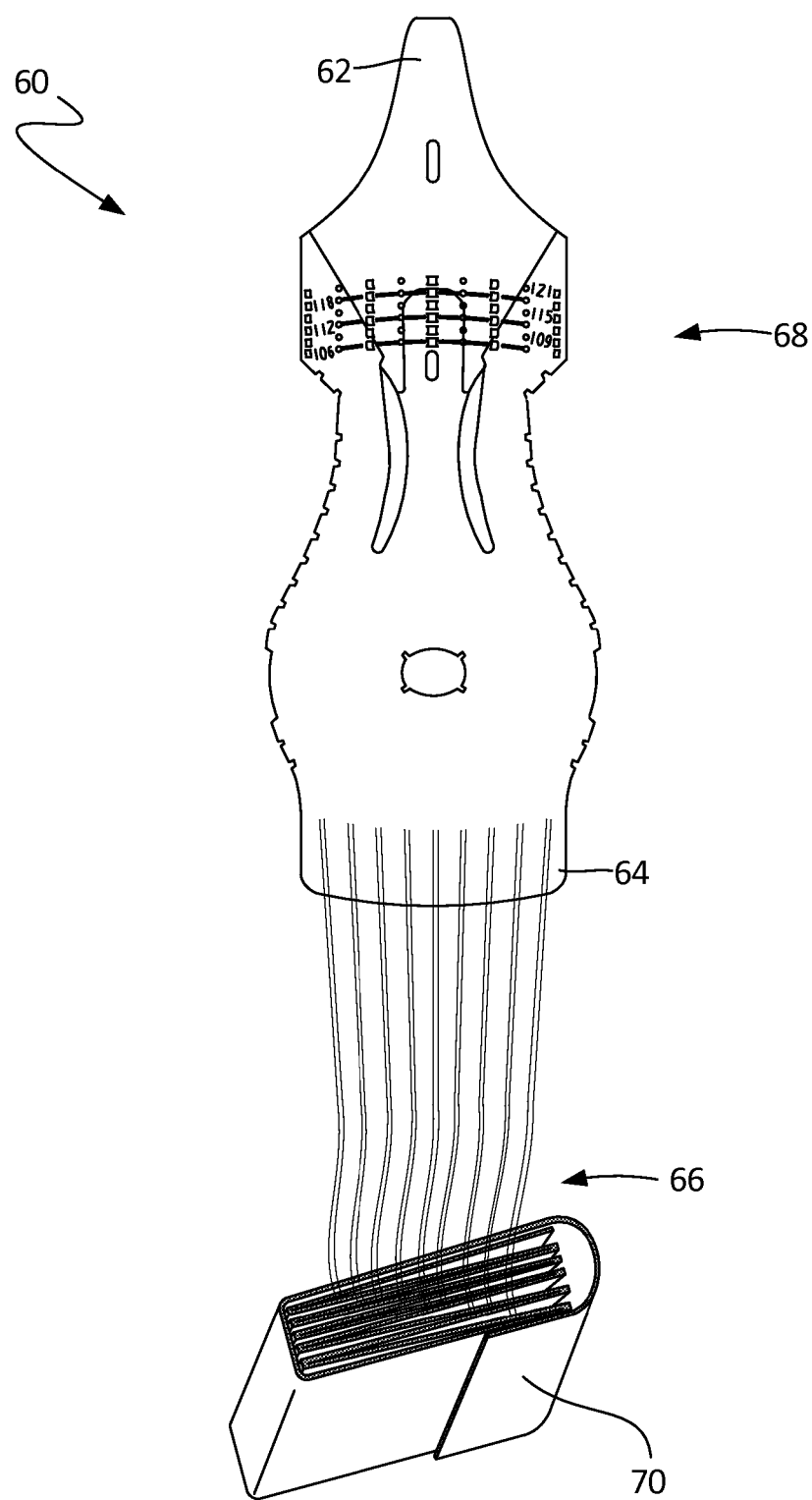
FIG. 2A is a front view of a wrap with a suture carrier, according to one embodiment.
Figure 2B:
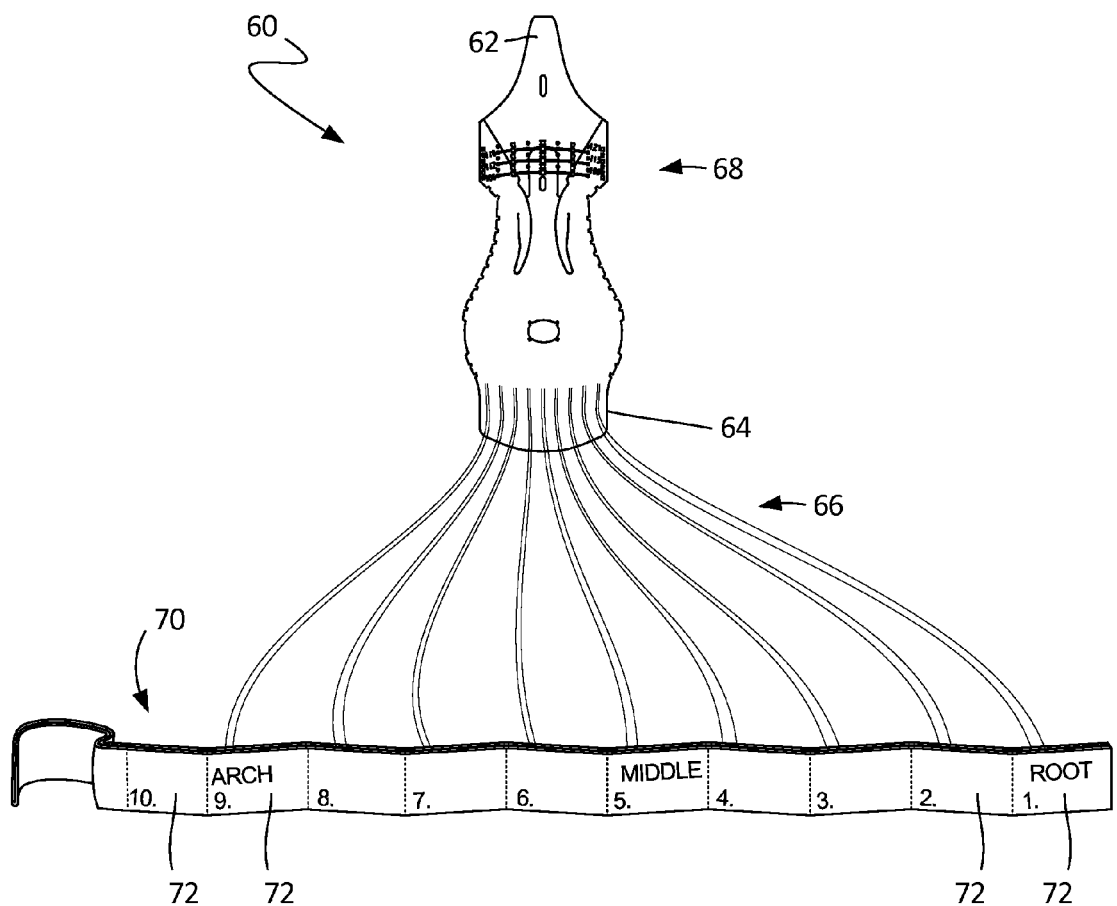
FIG. 2B is a front view of the wrap of FIG. 2A.
Figure 2C:
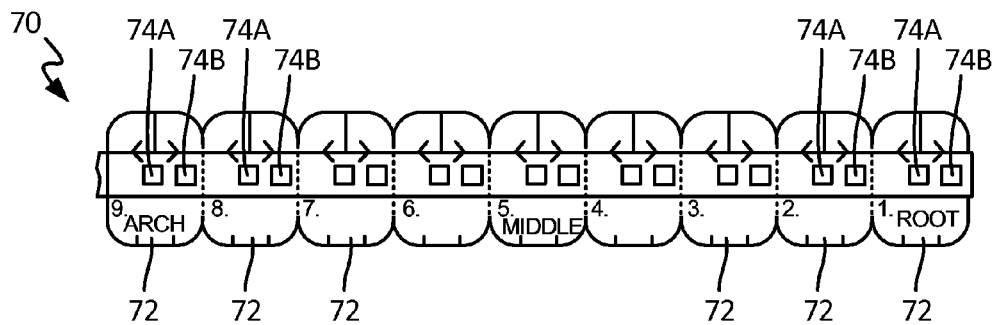
FIG. 2C is an expanded view of the suture carrier of the wrap of FIG. 2A.

FIGS. 2A, 2B, and 2C depict a second embodiment of a wrap 60. This wrap 60 has a first end 62 and a second end 64, with sutures 66 fixedly attached to the wrap 60 near the second end 64 and size markings 68 on the wrap 10 near the first end 62.

In this implementation, the wrap 60 also has a suture carrier 70. In FIG. 2A, the suture carrier 70 is shown in its collapsed or closed configuration, while in FIGS. 2B and 2C, the carrier 70 is shown in its expanded or open configuration. The carrier 70 is a foldable (or collapsible) elongate structure 70 made up of foldable sections 72. In one embodiment, the carrier 70 has the same number of foldable sections 72 as there are suture pairs. Further, the foldable sections 72 are joined to each other along foldable joints that are perforated (or otherwise easily separable) such that any combination of sections 72 can be removed from the carrier 70 to allow for easy and flexible placement during procedures and further to prevent tangling. Each foldable section 72 has two engagement structures 74A, 74B operably coupled to the section 72. Each of the engagement structures 74A, 74B is intended to receive and retain one of the needles (not shown) of one of the sutures 66. That is, each needle (not shown) of each suture 68 is inserted into an engagement structure 74A, 74B to retain the needle (not shown) in the engagement structure 74A, 74B. In one embodiment, the two engagement structures 74A, 74B are intended to receive one of the suture pairs, such that each foldable section 72 is configured to receive one of the pairs of sutures 66, with one of the sutures 66 being inserted into one of the engagement structures 74A and the other of the sutures 66 being inserted into the other structure 74B.

In one implementation, the foldable sections 72 can have printed text on each section 72 that indicates the sequential order of the suture pairs 66 attached or inserted through each section. This text can help to prevent tangling and guide correct installation order. In a further embodiment, printed text or some type of markings can be provided on certain sections 72 that represents or indicates the intended or target location on the wrap 60 that each suture pair would ideally or preferably be inserted, thereby helping to guide installation. For example, the text or markings can indicate that the pair of sutures 66 should be inserted at a location in the middle of the wrap 60, towards the root of the aorta, or towards the arch of the aorta.

In specific examples, the foldable sections 72 can be made of papers (such as, for example, bleached chemical thermomechanical pulp ("BCTMP")), plastics (such as, for example, JPP synthetic—a white mat biaxially oriented polypropylene sheet), or polyethylene sheets. Alternatively, the sections 72 can be made of any known cardboard-like material. The engagement structures 74A, 74B can be made of a foam (such as HT-513228 polyethylene foam), plastics, polyurethanes, silicones, or any other known material configured to receive and retain a needle.

In one implementation, the various wrap embodiments disclosed and contemplated herein can be produced from woven polyester or similar non-absorbable biostable and biocompatible material. Additional materials include polyethylene, polyurethane, segmented polycarbonates, ePTFE, and silicones. Alternatively, any known flexible material for use in medical devices can be used herein.

In accordance with one embodiment, the outer edges of the wrap can have material that has been treated, finished, coated, or designed to minimize trauma to any biological surfaces with which the wrap comes into contact. For example, the outer edges can be coated with a soft biocompatible, biostable polymer or elastomer. Alternatively, the outer edges can be made of a soft, stretchable fabric. These non-traumatic edges can thus reduce any trauma or damage to any biological surfaces during positioning of the wrap or once the wrap has been attached in place as desired.

Figure 3:
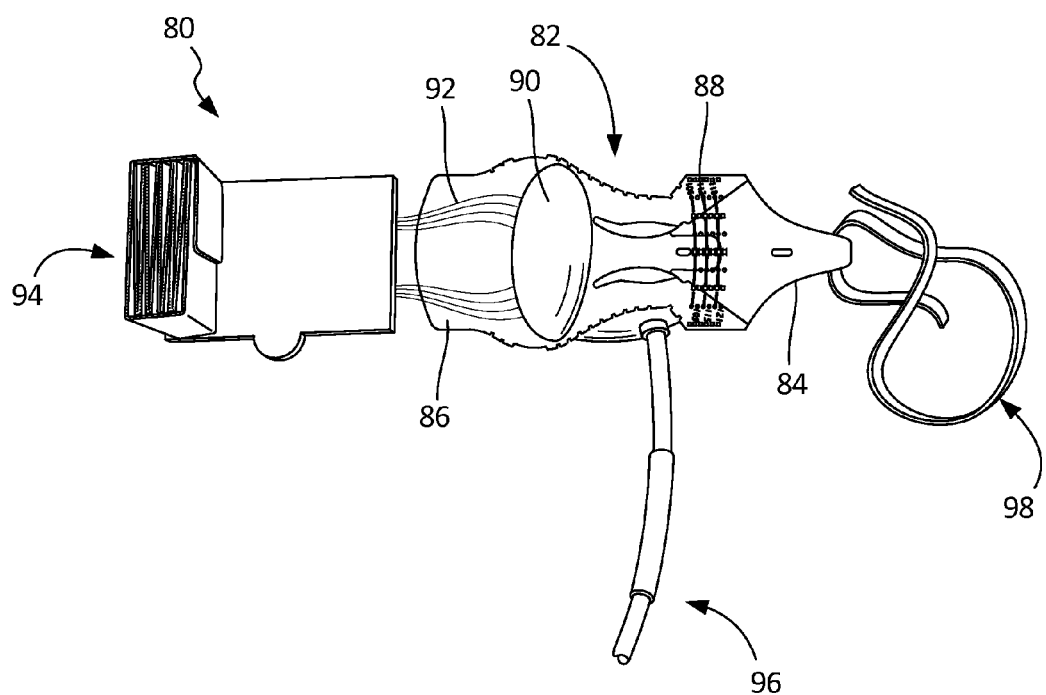
FIG. 3 is a front view of another wrap, according to a further embodiment.

Another embodiment of a wrap system 80 is depicted in FIG. 3. This system 80 has a wrap 82 with a first end 84, a second end 86, and size markings 88, a balloon 90, sutures 92, and a suture carrier 94. Further, the system 80 also has an interface line 96 that is coupled to the balloon 90 and allows for transfer of fluid between the balloon 90 and a pump (not shown) for purposes of inflating and deflating the balloon 90 during use. The interface line 96 can also provide for transmission of electrical and/or electronic signals via one or more wires. In addition, this implementation has a lead member 98 that is attached to the first end 84 of the wrap 82 to help insert or otherwise position the first end 84 during placement of the wrap 82. That is, the lead member 98 can be umbilical tape or any other relatively narrow elongate object that can be inserted behind the aorta of the patient more easily than the wrap 82 itself during implantation. Further, the lead member 98 can also be used for measurement of the aorta or other biological features of the patient during implantation.

It is understood that any of the wrap embodiments disclosed or contemplated herein can also include any of the wrap materials and/or configurations disclosed in U.S. Pat. Nos. 8,206,278 and 8,469,873, both of which are hereby incorporated herein by reference in their entireties.

In use, a wrap 100 can be positioned around a blood vessel such as an aorta 110 as shown in FIGS. 4-7.

Prior to positioning the wrap around the target blood vessel, the circumference of the target vessel is measured to determine the desired circumference of the wrap. Based on this measurement, the appropriate wrap can be selected (from a set of wraps as discussed above) and the appropriate set of attachments points (as described above) can be selected on that wrap.

Once the appropriate wrap is selected, the suture carrier (such as the carrier 70 of FIGS. 2A-2C) is opened as shown in FIGS. 2B and 2C to access the sutures. Alternatively, the suture carrier (such as carrier 70) can be opened after the first end 102 of the wrap 100 is positioned around the back side of the aorta 110 as discussed below. Once the carrier (such as carrier 70) is opened, the surgeon or user can select the first desired pair of sutures for insertion through the desired location on the size markings (such as the markings 18 depicted in FIGS. 1A-1C) as discussed in further detail below.

Figure 4:
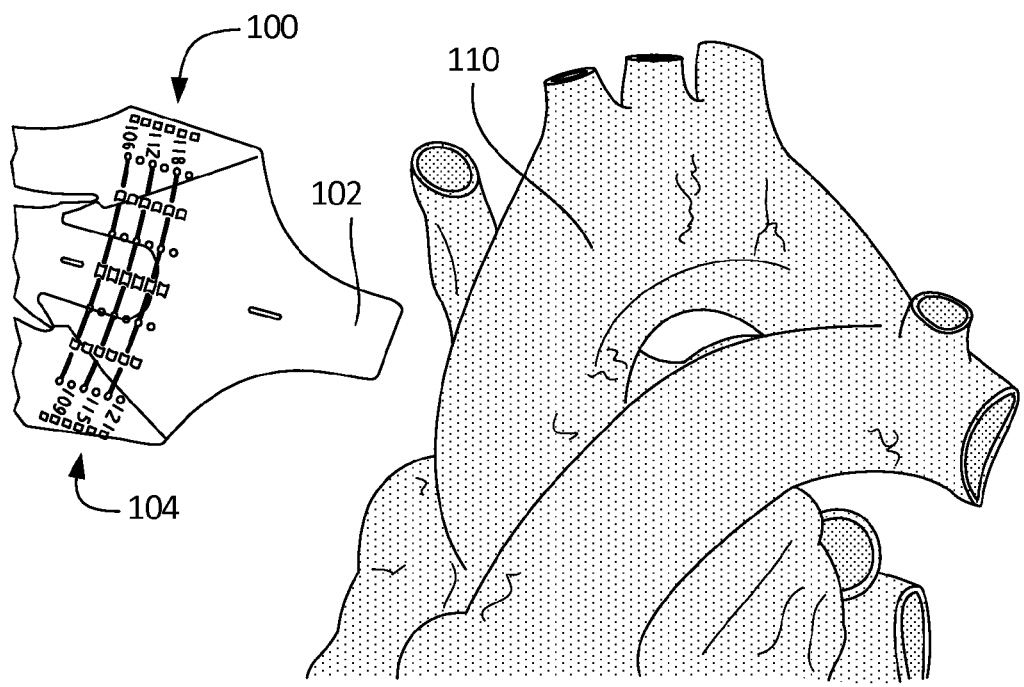
FIG. 4 is a perspective view of a step of a method of attaching a wrap to an aorta, according to one embodiment.

The first end 102 of the selected wrap 100 is positioned to be inserted behind the vessel 110 (in this case, the aorta 110)

as best shown in FIG. 4. In those embodiments in which a lead member (such as lead member 98 discussed above) is attached to the first end 102 of the wrap 100, the lead member can be inserted behind the aorta 110 to more easily pull the first end 102 of the wrap 100 distally.

Figure 5:
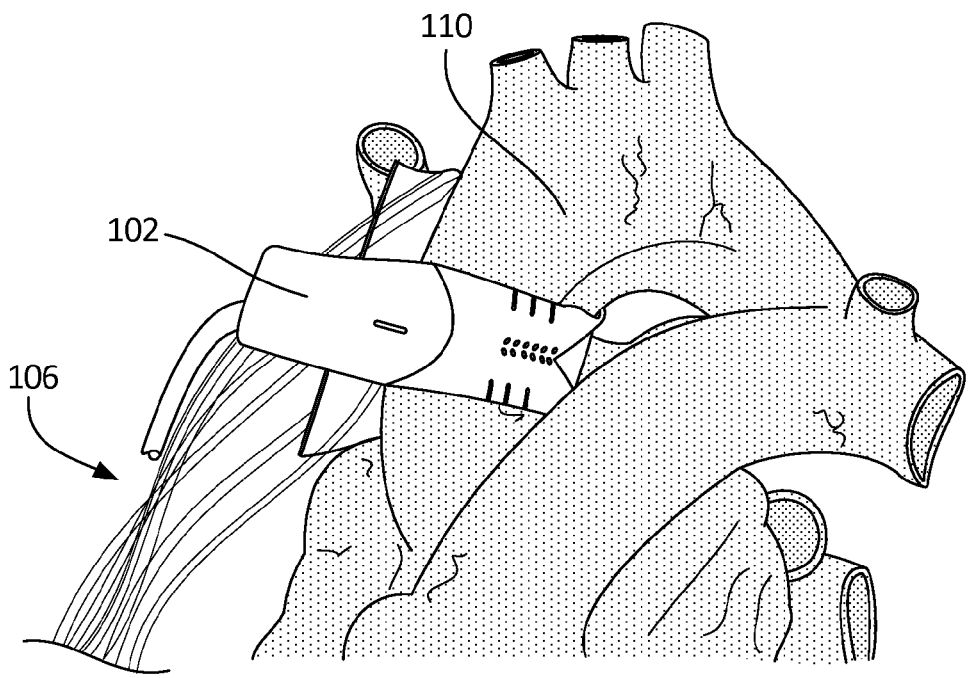
FIG. 5 is a perspective view of another step of a method of attaching a wrap to an aorta, according to one embodiment.

Whether a lead member (such as lead member 98) is used or not, the first end 102 of the wrap 100 is positioned around the back side of the aorta 110 and pulled toward the user on the other side as shown in FIG. 5, thereby positioning the wrap 100 around the aorta 110.

Figure 6:
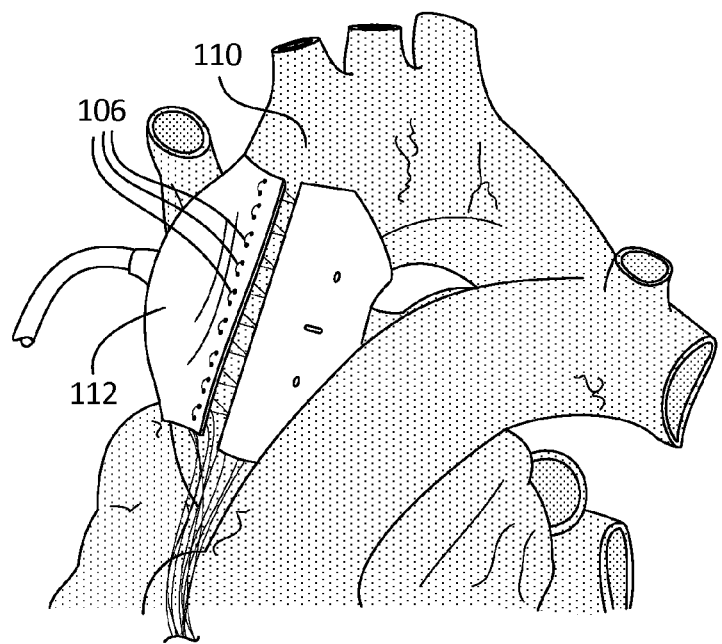
FIG. 6 is a perspective view of a further step of a method of attaching a wrap to an aorta, according to one embodiment.

At this point, a vessel deforming component 112 (such as a balloon 112) can be positioned between the wrap 100 and the aorta 110 in the desired position (as shown, for example, in FIG. 6). Alternatively, the vessel deforming component 112 could be positioned with the wrap 100 when the wrap 100 is inserted around the aorta 110 such that both the vessel deforming component 112 and wrap 100 are positioned together. In a further alternative, the vessel deforming component 112 is previously attached or otherwise coupled to the wrap 100.

Once the wrap 100 and the vessel deforming component 112 are positioned as desired, the sutures 106 are inserted through the chosen set of attachment points on the size markings 104. That is, each of the pairs of sutures 106—one after another—is removed from the engagement structures (such as engagement structures 74A, 74B discussed above) of the carrier (such as carrier 70) and is inserted through the wrap 100 at the appropriate attachment point on the markings 104. As described above, the needle of the one of the sutures 106 of each pair is inserted through the wrap 100 on one side of the corresponding attachment point (such as one of the nine indicia described above and in FIG. 1C), and then the needle of the second of the pair of sutures 106 is inserted on the other side of the same attachment point. Alternatively, the pair of sutures 106 are inserted into any type of indicia that might be provided in any known fashion. Once the two sutures 106 of the pair are both inserted through the wrap 100, the needles are removed and the newly needle-less ends of the two sutures 106 are tied or otherwise fastened together (and the excess lengths of the sutures 106 removed) as best shown in FIG. 7.

This process is repeated for each of the suture pairs, with the surgeon or user sequentially selecting and inserting each of the desired pairs of sutures into the markings (such as markings 18) in the desired order until the wrap 100 is secured around the aorta 110 and the sutures 106 are secured in the wrap 100. In one exemplary embodiment, the sequential order can be selecting the middle pair of sutures on the carrier, following by selecting the pairs on the ends of the carrier, and then sequentially selecting the remaining pairs. Alternatively, any order can be used.

Alternatively, the sutures 106 can be attached in any known fashion using the size markings 104 to secure the wrap 100 around the target vessel.

Figure 7:
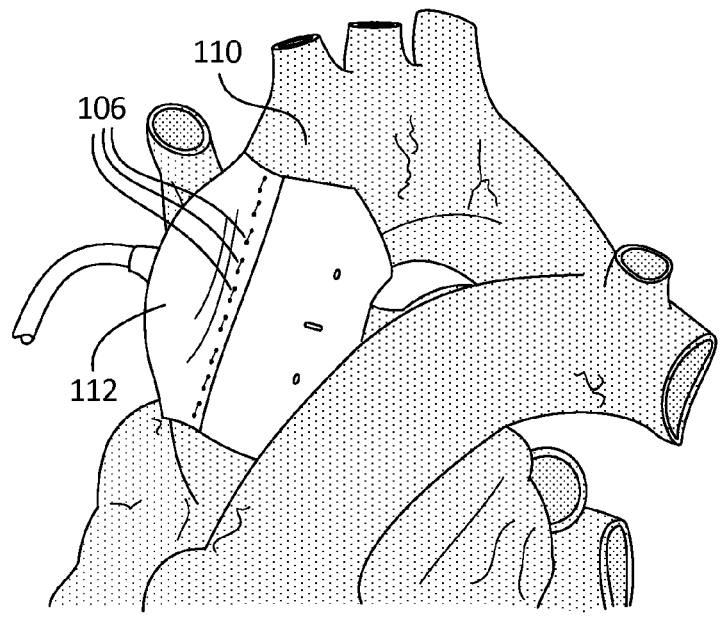
FIG. 7 is a perspective view of a wrap attached to an aorta, according to one embodiment.

Once the sutures 106 are tied and the excess length of each suture 106 removed, any excess length of the wrap 100 is removed as shown in FIG. 7.

While multiple embodiments are disclosed, still other embodiments will be apparent to those skilled in the art from the above detailed description, which shows and describes illustrative embodiments. As will be realized, these various embodiments are capable of modifications in various obvious aspects, all without departing from the spirit and scope of the inventions. Accordingly, the drawings and detailed description are to be regarded as illustrative in nature and not restrictive.

What is claimed is:

1. A system for coupling a vessel deforming component to a blood vessel, the system comprising:
    (a) a wrap comprising:
        (i) a body;
        (ii) size markings disposed on the body;
        (iii) a plurality of pairs of sutures extending from a proximal end of the body, wherein each of the sutures comprises a needle disposed at a distal end of the suture; and
        (iv) a lead member coupled to a distal end of the body; and
    (b) a vessel deforming component operably coupled to the wrap.

2. The system of claim 1, further comprising a suture carrier comprising:
    (a) an elongate body;
    (b) a plurality of foldable sections defined in the elongate body;
    (c) at least one engagement structure associated with each foldable section, wherein each of the at least one engagement structures is removably coupleable with the needle of one of the sutures of the plurality of pairs of sutures; and
    (d) insertion markings disposed on at least one of the foldable sections, wherein the insertion markings are configured to indicate insertion positions of the plurality of pairs of sutures.

3. The system of claim 1, wherein each pair comprises a color that is different from either adjacent pair of sutures.

4. The system of claim 1, wherein the body comprises non-traumatic outer edges.

5. The system of claim 4, wherein the non-traumatic edges comprise a coated polymer, a coated elastomer, or a soft, stretchable fabric.

6. A system for coupling a vessel deforming component to a blood vessel, the system comprising:
    (a) a wrap comprising:
        (i) a body;
        (ii) size markings disposed on the body;
        (iii) a plurality of sutures extending from a proximal end of the body; and
        (iv) a lead member coupled to a distal end of the body; and
    (b) a suture carrier comprising an elongate structure comprising a plurality of foldable sections, wherein each of the foldable sections comprises at least one engagement structure.

7. The system of claim 6, wherein the plurality of sutures are arranged in a plurality of pairs, wherein each suture comprises a needle disposed at a distal end of the suture.

8. The system of claim 7, wherein each pair comprises a color that is different from either adjacent pair of sutures.

9. The system of claim 6, wherein at least one of the foldable sections comprises insertion markings configured to indicate insertion positions of the plurality of pairs of sutures.

10. The system of claim 6, wherein the body comprises non-traumatic outer edges.

11. The system of claim 10, wherein the non-traumatic edges comprise a coated polymer, a coated elastomer, or a soft, stretchable fabric.

12. The system of claim 6, further comprising a vessel deforming component operably coupled to the wrap.

13. A method of coupling a vessel deforming component to a blood vessel, the method comprising:

positioning a lead member behind an aorta of a patient, wherein the lead member is operably coupled to a distal end of a wrap, wherein the wrap comprises:
  (a) a body;
  (b) size markings disposed on the body; and
  (c) a plurality of sutures extending from a proximal end of the body;
urging the lead member distally around the aorta such that the wrap is positioned around the aorta;
sequentially removing sutures of the plurality of sutures from engagement structures in a suture carrier and sequentially inserting the sutures into a desired location on the size markings; and
tightening the sutures.

14. The method of claim 13, further comprising removing the lead member from the wrap after urging the lead member distally around the aorta.

15. The method of claim 13, further comprising folding the body of the wrap to narrow a width of the body prior to urging the lead member distally around the aorta and then unfolding the body of the wrap after urging the lead member distally around the aorta.

16. The method of claim 13, further comprising opening the suture carrier and separating at least one foldable section from the suture carrier prior to sequentially removing sutures.

17. The method of claim 13, further comprising cutting excess length of the sutures and excess portions of the body after tightening the sutures.

* * * * *